United States Patent
Taniguchi et al.

[11] Patent Number: 5,311,275
[45] Date of Patent: May 10, 1994

[54] APPARATUS AND METHOD FOR DETECTING PARTICLES ON A SUBSTRATE

[75] Inventors: Minoru Taniguchi; Masaaki Ishihara; Takashi Hagiwara, all of Miyanohigashi, Japan

[73] Assignee: Horiba, Ltd., Kyoto, Japan

[21] Appl. No.: 922,057

[22] Filed: Jul. 29, 1992

[30] Foreign Application Priority Data

Jul. 30, 1991 [JP] Japan ................ 3-067258[U]

[51] Int. Cl.⁵ ......................................... G01N 21/00
[52] U.S. Cl. .................................. 356/237; 356/400; 250/561; 250/563
[58] Field of Search ............... 356/237, 431, 375, 150, 356/154, 338, 400; 250/563, 572, 561

[56] References Cited

U.S. PATENT DOCUMENTS

| | | |
|---|---|---|
| 4,468,120 | 8/1984 | Tanimoto et al. .............. 356/237 |
| 4,549,206 | 10/1985 | Suzuki et al. .................. 250/563 |
| 4,596,467 | 6/1986 | Bartelt ............................ 356/363 |
| 4,610,541 | 9/1986 | Tanimoto et al. .............. 356/237 |
| 4,693,608 | 9/1987 | Kitagawa et al. .............. 356/237 |
| 4,829,175 | 5/1989 | Goto et al. ..................... 250/236 |
| 4,889,998 | 12/1989 | Hayano et al. ................. 250/563 |
| 4,898,471 | 2/1990 | Stonestrom et al. ........... 356/237 |
| 4,902,131 | 2/1990 | Yamazaki et al. ............. 356/237 |
| 4,938,600 | 7/1990 | Into ................................. 356/400 |
| 4,971,445 | 11/1990 | Sato et al. ...................... 356/376 |
| 4,999,510 | 3/1991 | Hayano et al. ................. 250/571 |

*Primary Examiner*—Robert J. Warden
*Assistant Examiner*—Hien Tran
*Attorney, Agent, or Firm*—Price, Gess & Ubell

[57] ABSTRACT

An apparatus and method for observing the location of minute particles on a substrate and adjusting for any inclination of the substrate surface is provided. A support station can mount a substrate for movement in both the X and Y planes and in the vertical plane. A laser scanning optical device can determine the locations of minute particles. The coordinates of any inclination of support surface is determined and is used to vary the particle positions so that a subsequent examination by a microscope will be easily accomplished with an in-focus position.

7 Claims, 5 Drawing Sheets

APPARATUS AND METHOD FOR DETECTING PARTICLES ON A SUBSTRATE

BACKGROUND OF THE INVENTION

1. Field of the Invention

The present invention relates to an apparatus for detecting unwanted particles adhering to surfaces of substrates to be inspected, such as reticles and masks used for printing circuit patterns on semiconductor wafers, for example, in the process of producing LSI (large-scale integrated) product wafers, on which circuit patterns are formed, or substrates for use in liquid crystal displays and more particularly an apparatus and method of specifying a size and location where the particles are adhered to enable a visual inspection.

2. Description of Related Art

An apparatus for detecting particles, in which an inspection stage for placing a substrate to be inspected thereon is adapted to linearly move between a particle-inspecting position and a particle-observing position. Such apparatus have been used with laser beams having an appointed angle of polarization, incident upon a surface of the substrate to be inspected, while being scanned by means of a beam-scanning mirror. Reflected and scattered beams from the surface of the substrate to be inspected are incident upon a detector optical system to detect any existence of particles on the surface of the substrate and to further measure a size of the particles on the basis of the results of detection of the reflected and scattered beams. A particle-observing position where the detected particles can be observed and confirmed by means of a microscope has also been known.

A problem has existed in that some inclination may be produced in a flat surface of the inspection stage to even a slight extent though the tolerance of fabricating accuracy and an assembling accuracy of parts. When the substrate to be inspected is placed on an inspection stage having such an inclination, the substrate to be inspected is also inclined. Generally, a substrate to be inspected, which is an object to be observed, has been considered to be uniformly flat or horizontal and the focus of a microscope has been adjusted at merely one point on the substrate to be inspected, so that the same focus condition must be shifted for other particles because the focus has been adjusted for only one particle position, if the substrate to be inspected is moved when the particles detected by the application of the laser beam are enlargedly observed and confirmed by means of the microscope.

In order to prevent a problem of a focus shift, the focus has been further detected to a high level by an optical method but such an apparatus has been complicated in construction and control.

SUMMARY OF THE INVENTION

The present invention has been achieved by paying attention to the above described matters and it is an object of the present invention to provide a relatively inexpensive apparatus for detecting particles that is also capable of observing and confirming such particles under a condition that the focus is always adjusted to the particles on a substrate to be inspected even though the substrate to be inspected is inclined due to an inclination of an inspection stage.

In order to achieve the above described object, in an apparatus for detecting particles according to the present invention, the inclination of a flat surface of the substrate to be inspected is determined on the basis of three-dimensional coordinates at three optional points on the surface of the substrate to be inspected, while positioned on an inspection stage at a particle-observing position. These coordinate values are memorized as a flat surface inclination constant of the apparatus and the focus of a microscope is adjusted to the particles on the basis of its flat surface inclination.

The inclination of the flat surface of the inspection stage can be obtained on the basis of three-dimensional coordinates of optional three points on the substrate to be inspected, placed on the inspection stage. Accordingly, if the inclination of this flat surface is memorized as a constant peculiar to the apparatus and the focus of the microscope is adjusted to the particles on the basis of the flat surface inclination constant, the particles can always be clearly confirmed at a correct focal position. Such an apparatus is not complicated in construction and control.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an apparatus and method for detecting particles on a substrate.

The preferred embodiments of the present invention will be described below with reference to the drawings.

Figure 1:
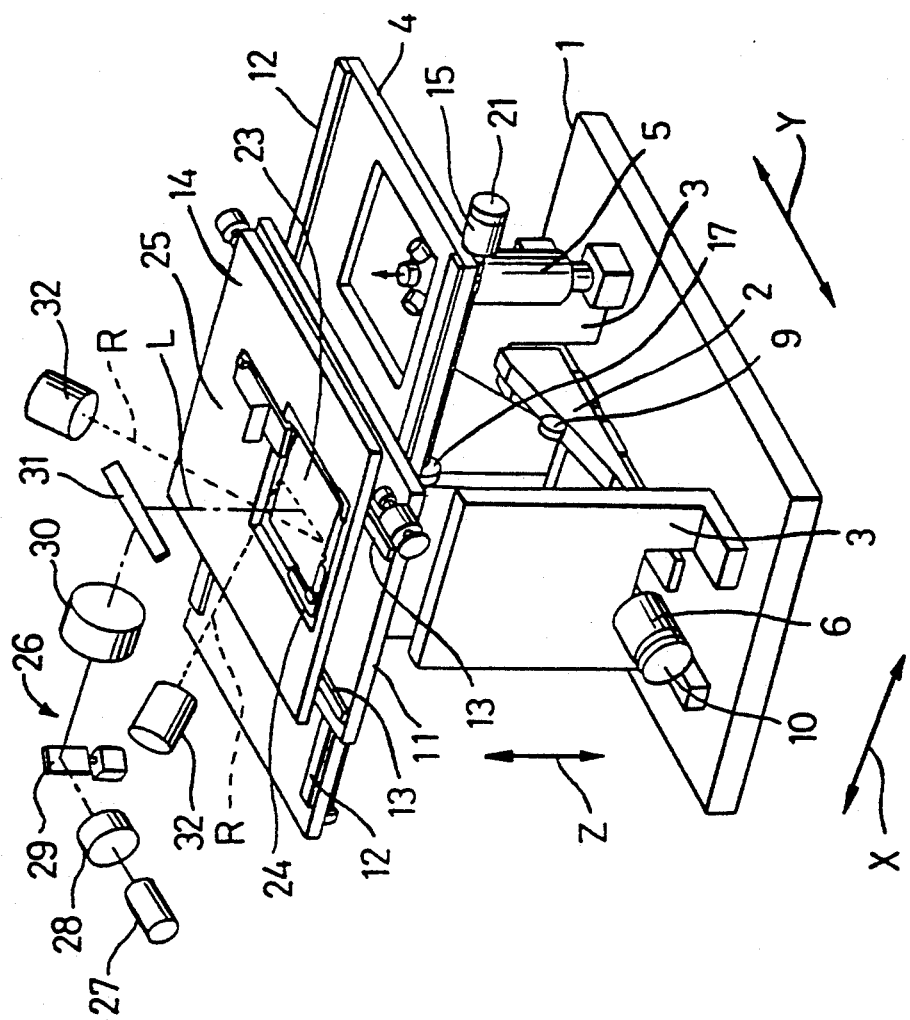
FIG. 1 is a perspective view showing essential components in an apparatus for detecting particles according to the present invention.
Figure 2:
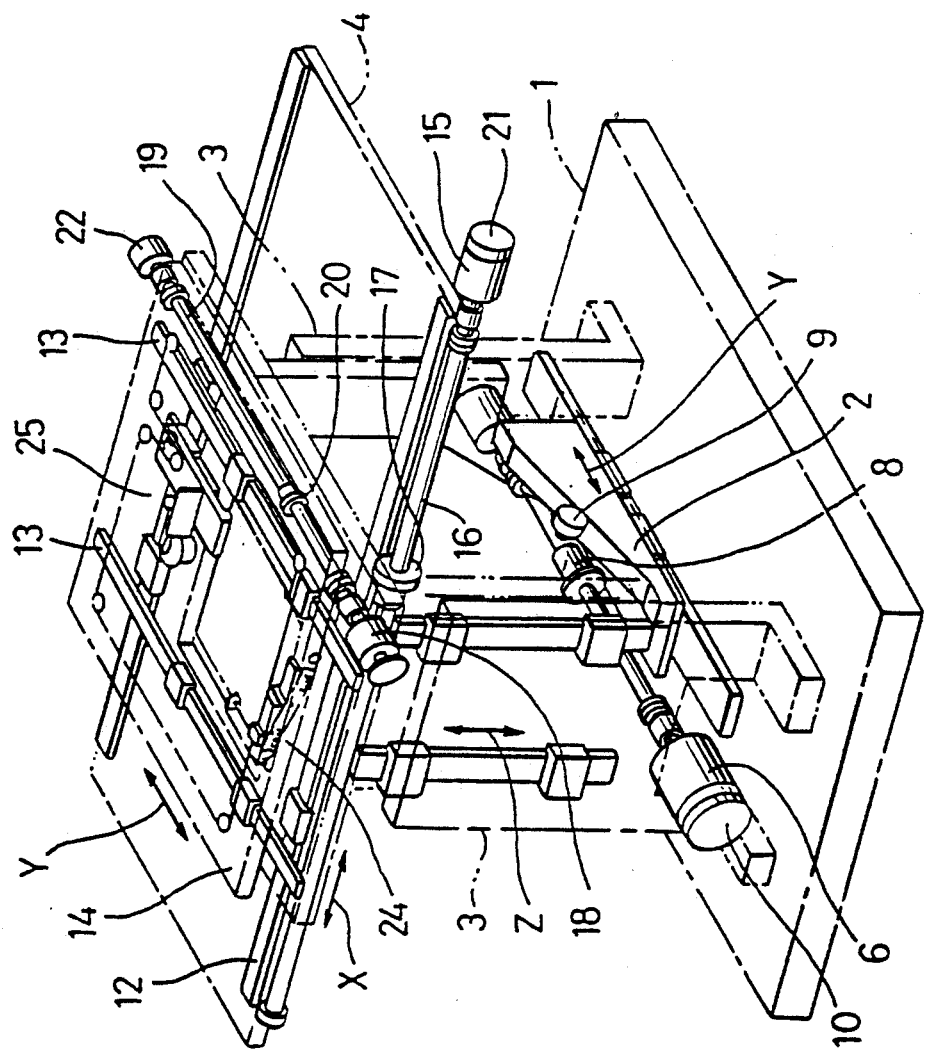
FIG. 2 is a perspective view showing a driving system in the apparatus according to the present invention.
Figure 3:
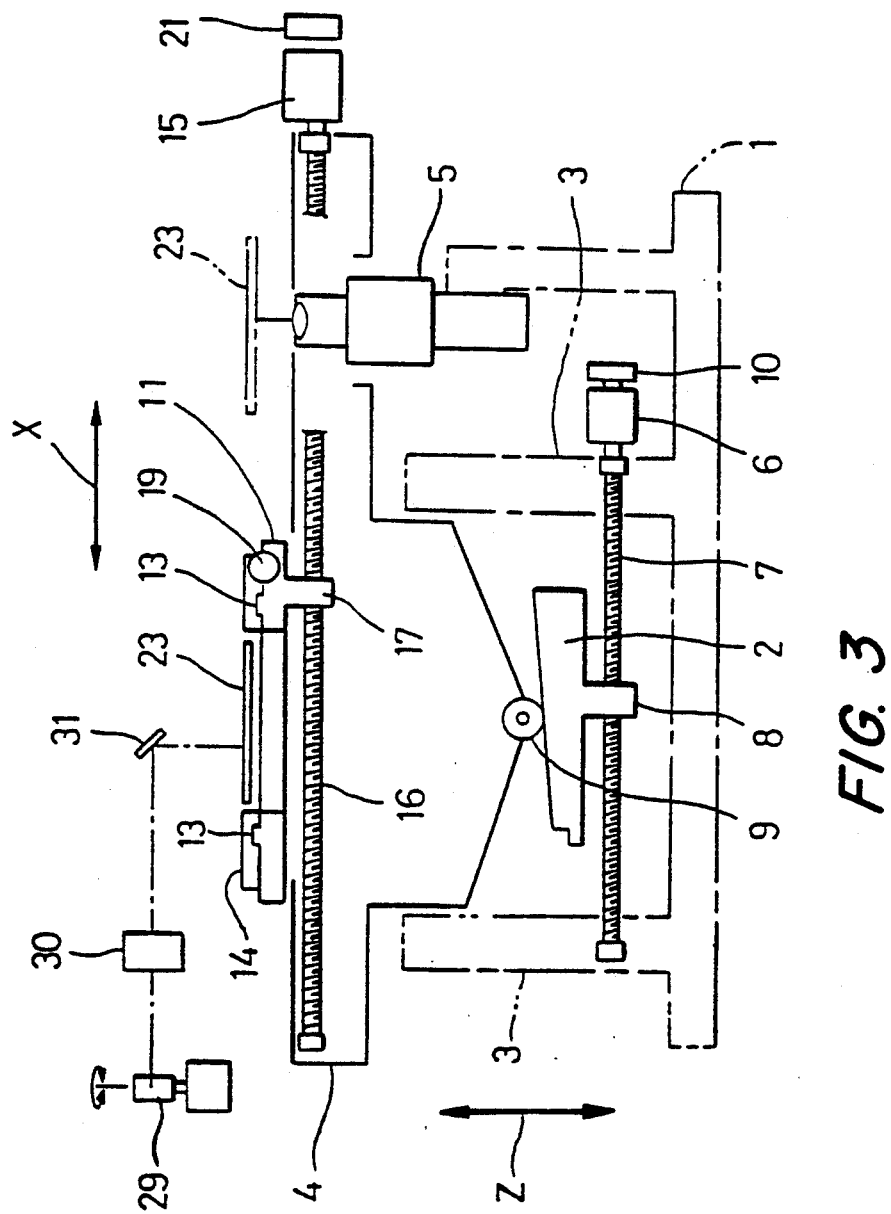
FIG. 3 is a drawing showing essential components in the driving system in the directions of X and Z in the apparatus according to the present invention.
Figure 4:
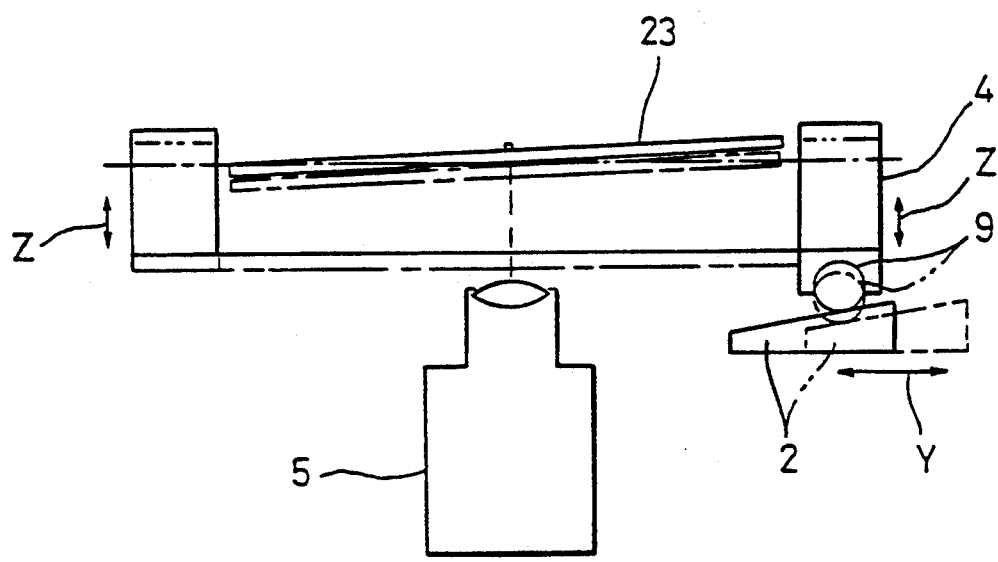
FIG. 4 is a drawing showing essential components in the driving system in the direction of Z in the apparatus according to the present invention.

Referring to FIG. 1 and FIG. 2, reference numeral 1 designates a fixed platform or base provided with a trestle 4 capable of being elevated in the direction of Z (the up and down, or vertical direction) along a standing member 3 and a cam 2 capable of driving in the direction of Y (the back and forth direction) relative to a microscope 5. That is to say, the fixed base 1 is provided with a threaded shaft 7 connected with a pulse motor 6 on one end thereof and aligned in the direction of Y. The cam 2 is provided with a threaded nut member 8, which engages with the threaded shaft 7, and a cam follower 9 is pivoted on the cam 2 below the trestle 4, as shown in FIG. 3. The pulse motor 6 is further provided with a rotary encoder 10 to monitor rotational movement.

Reference numeral 11 designates a slide base capable of being driven in the direction of X (the right and left direction) along a guide rail 12, which is provided on an upper surface of the trestle 4. An inspection stage 14, which is driven in the direction of Y along a guide rail 13, is provided on an upper surface of the slide base 11, is placed on the slide base 11. The inspection stage 14 is adapted to be movable between a particle-inspecting position and a particle-observing position with a movement of the slide base 11.

As shown also in FIG. 3, a threaded shaft 16, which is connected with a DC servo motor 15 at one side thereof, is aligned in the direction of X on the trestle 4 and a nut member 17, engaged with the threaded shaft 16, is provide on the slide base 11. In addition, a nut member 20, which is connected with a pulse motor 18 at one end side thereof and engaged with a threaded shaft 19 extending in the direction of Y, is provided on a lower surface of the inspection stage 14. Rotary encoders 21 and 22 are provided on the DC servo motor 15 and pulse motor 18, respectively.

A fixed member 24 and a movable member 25 are provided on an upper surface of the inspection stage 14 for fixing a substrate to be inspected 23, such as reticles, used for printing a circuit pattern on, for example, a semiconductor wafer at an appointed position.

Reference numeral 26 designates an incident optical system comprising, for example, a He-Ne laser transmitter 27, transmitting a laser beam L, having an appointed angle of polarization, a beam expander 28, a beam-scanning mirror 29, scanning the laser beam in the direction of Y, a collecting lens 30 for collecting the laser beam L from the beam-scanning mirror 29 to make the laser beam L incident upon a surface of the substrate to be inspected 23, and a mirror 31 for making the laser beam L, incident upon the substrate to be inspected 23 from an inclined upper portion in the direction of X with scanning. In addition, reference numeral 32 designates two detective optical systems arranged at a suitable interval in an inclined upper portion in the direction of Y and comprising a collecting lens, a slit, an analyzer for cutting a specified straight polarized component and an optical detector arranged in the order describe, respectively, for detecting reflected and scattered beams R, produced when the laser beam L is incident upon particles on the substrate to be inspected 23, although they are not shown in detail.

Figure 5:
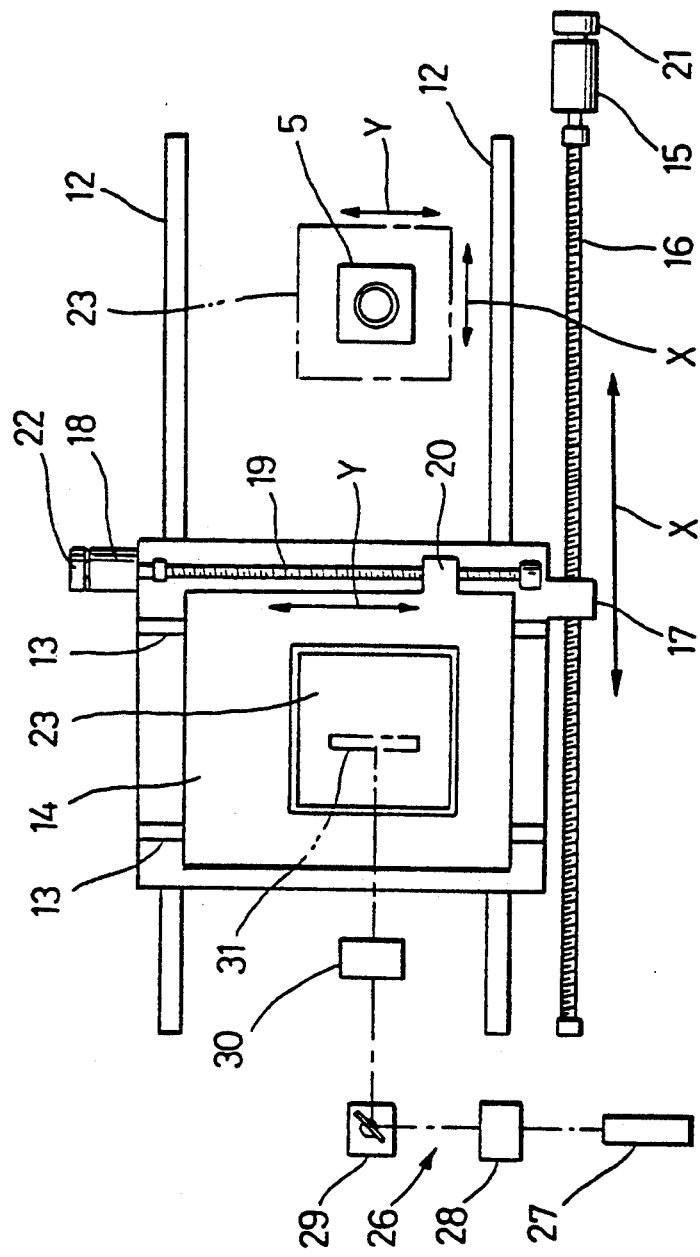
FIG. 5 is a drawing showing essential components in the driving system in the directions of X and Y in the apparatus according to the present invention.

Accordingly, with the apparatus for detecting particles having the above described construction, as shown in FIG. 1, the substrate to be inspected 23 is placed on the inspection stage 14 as the particle-inspection position, a laser beam L having an appointed angle of polarization, is incident upon the surface of the substrate to be inspected 23, while being scanned by means of the beam-scanning mirror 29, the reflected and scattered beams R from the surface of the substrate to be inspected 23 at that time being incident upon the detecting optical systems 32, and the existence of any particles on the surface of the substrate to be inspected 23 are detected and their sizes are measured on the basis of the results of detection of the reflected and scattered beams R by the detecting optical systems 32. In the case, where the substrate to be inspected 23 is positioned at the particle-observing position, as shown by an imaginary line in FIG. 3 and FIG. 5, respectively, the detected particles can be magnified by means of the microscope 5 to observe and confirm them. Although not shown in FIG. 1 a second microscope can be positioned on the other side of the microscope 5 to enable both an upper and lower surface inspection of the substrate 23.

However, in order to magnify the detected particles, it is necessary that the inspection stage 14 is moved to a particle-observing position, at which the microscope 5 is provided. The substrate to be inspected 23 is placed on the inspection stage 14 and the inspection stage 14 is moved in the right and left direction and the rear and front direction to adjust for the detected positions of any particles on the substrate to be inspected 23, and the trestle 4 supporting the inspection stage 14 is moved in an up and down direction to adjust for the focus position on the particles.

To achieve an in-focus position according to the present invention, an optional three separate points of positions are selected on the surface of the substrate to be inspected 23 under the condition that the inspection stage 14 is set at the particle-observing position. Any inclination of the flat surface of the substrate to be inspected 23 is accordingly determined on the basis of the three-dimensional coordinates, established from the three separate points, that is, their positions (length, width and height) in the directions of X, Y, and Z. Thus, the inclination of the plane defined by the three points is calculated and memorized as the flat surface inclination constant of the apparatus.

Assuming that the three points on the substrate are the observing point $P_0$ and the tilt-correcting values $P_1$, $P_2$, their coordinates can be determined as follows:

$P_0$: $(x_0, y_0, z_0)$
$P_1$: $(x_1, y_1, z_1)$
$P_2$: $(x_2, y_2, z_2)$

Furthermore, the above described $P_0$, $P_1$, $P_2$ are the absolute coordinates with the fundamental point of the stage as the standard.

And, the focusing position (Z-axis) z of the microscope at an optional position (x, y) of the stage is determined by the following expression:

$$z = A(x-x_0) + B(y-y_0) + z_0$$

wherein A, B are plane inclination constants (correction factors) and expressed by the following expressions, respectively.

$$A = \frac{\{(z_0 - z_1)(y_0 - y_2) - (z_0 - z_2)(y_0 - y_1)\}}{\{(x_0 - x_1)(y_0 - y_2) - (x_0 - x_2)(y_0 - y_1)\}}$$

$$B = \frac{\{(z_0 - z_2)(x_0 - x_1) - (z_0 - z_1)(x_0 - x_2)\}}{\{(x_0 - x_1)(y_0 - y_2) - (x_0 - x_2)(y_0 - y_1)\}}$$

The detected location of a particle on the substrate from the laser optical system detectors 32 can be coordinated relative to the known location of the microscope 5 at the particle-observing position and the inclination of the substrate plane can define the desired movement in a vertical plane, Z.

The longitudinal coordinate and the lateral coordinate disclose the quantity of movement in the direction of Y and X, respectively. In addition, the height is a distance to an object lens of the microscope 5.

When the detected particles are to be magnified for observation and confirmation, the movement of the trestle 4 in the above described respective directions are appropriately corrected on the basis of the flat surface inclination constant. In addition, it is preferable that the three points be selected from a relatively wide range on the substrate 23 to be inspected so that any error can be reduced.

The trestle 4 can be accurately moved in the optional directions of X and Y, respectively, and calculating the inclination of the substrate 23 to be inspected in the apparatus with trigonometry principles, the particles on the substrate to be inspected 23 can always be clearly confirmed at the correct focal position.

As can be appreciated, a computer control circuit (not shown) can store the inclination constants and automatically correct the focus position of each determined particle at the inspection stage. The computer control circuit can appropriately control the motors in coordination with the encoders to align the substrate 23 for inspection so that the detected position of any minute particle can be correctly positioned at an observation station in front of the microscope 5 with any substrate inclination taken into account so that the microscope 5 will immediately be in focus. As can be readily appreciated, this control system can automate a focusing operation without requiring significant hardware and expensive optical monitoring systems. As above described, according to the present invention, even though the substrate to be inspected is inclined due to an inclination of the inspection stage, the particles can be observed and confirmed under the condition that the focus will always be accurately adjusted to the particles on the substrate to be inspected. According to the present invention, it is not required to detect the focus by a subsequent optical method, so that the apparatus is simplified in construction and control and can be inexpensively constructed.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An apparatus for observing the location of minute particles on a substrate, comprising:
   means for moving a substrate;
   means for determining any inclination of a substrate surface relative to a predetermined plane and providing data defining coordinates of inclination;
   means for determining a location of any particles on a substrate and providing data defining the coordinates of such particles;
   means for magnifying the particles to permit observation including means for defining a focal plane in which the particles are in focus, and
   means for activating the moving means in accordance with the data of the coordinates of a particle and the data of the coordinates of inclination to position the substrate within the focal plane of the magnifying means to enable an observer to view an enlargement of a particle in an in-focus position.

2. The apparatus of claim 1 wherein the means for activating includes motors and encoders for driving the moving means.

3. The apparatus of claim 2 wherein the means for moving the substrate includes a cam, a cam follower and guide rails wherein the can alters the height of the substrate with an interaction with the cam follower and the guide rails define movements in an X and Y direction.

4. The apparatus of claim 3 wherein the means for determining the location of particles includes a scanning laser and a pair of optical detectors for receiving laser light after being incident with the substrate.

5. The apparatus of claim 3 wherein the means for magnifying includes a microscope mounted below the substrate.

6. An apparatus for observing the location of minute particles on a substrate, comprising:
   a base member;
   substrate mounting means for movably mounting a substrate including guide rails for defining movements in a horizontal X and Y plane and a cam and cam follower for defining movements in a vertical Z plane;
   means for moving the substrate including electric motors and encoders for monitoring the movement of the motors;
   means for providing data of coordinates of any inclination of a substrate surface relative to a predetermined plane;
   means for determining a location of any particles on a substrate and providing data defining the coordinates of such particles including a scanning laser to contact the substrate surface and detector means to receive the laser light after incidence with the substrate surface;
   means for magnifying the particles including means for defining a focal plane, and
   means for activating the electric motors and encoders in accordance with the data of the coordinates of a particle an the data of the coordinates of inclination to position the substrate within the focal plane of the magnifying means to enable an observer to view an enlargement of particles in an in-focus position.

7. A method of observing minute particles on a substrate with a magnifying device having a focal plane at a predetermined position, comprising the steps of:
   determining any inclination of a substrate surface relative to a predetermined plane containing the substrate and providing data defining coordinates of inclination;
   scanning the substrate surface with a laser beam;
   determining locations of any particles on the substrate form contact of the laser beam with particles and providing data defining the coordinates of such particles;
   calculating an appropriate movement of the substrate to a focal plane based on the data of the coordinates of inclination and data of the coordinates of a particle;
   moving the substrate based on the calculated results, and
   observing the minute particle.

* * * * *